United States Patent [19]

Stroosnyder

[11] Patent Number: 5,587,581

[45] Date of Patent: Dec. 24, 1996

[54] METHOD AND AN APPARATUS FOR AN AIR SAMPLE ANALYSIS

[75] Inventor: Peter C. Stroosnyder, Finksburg, Md.

[73] Assignee: Environmental Technologies Group, Inc., Baltimore, Md.

[21] Appl. No.: 509,382

[22] Filed: Jul. 31, 1995

[51] Int. Cl.⁶ ............................. B01D 59/44; H01J 49/00
[52] U.S. Cl. .................................. 250/287; 250/282
[58] Field of Search ..................... 250/282, 286, 250/287

[56] References Cited

U.S. PATENT DOCUMENTS

| | | | |
|---|---|---|---|
| 4,855,595 | 8/1989 | Blanchard | 250/286 |
| 5,109,157 | 4/1992 | Loen | 250/287 |

Primary Examiner—Bruce C. Anderson
Attorney, Agent, or Firm—Leonard Bloom

[57] ABSTRACT

In an apparatus for an air sample analysis, employing a dual polarity Ion Mobility Spectrometer (IMS), a method for stabilizing equilibrium conditions associated with the switching of the electric fields in the IMS cell comprises the steps of modulating a duty cycle of the electric field at the shutter grid located between the reactor region and the drift region of the IMS cell. During the switching of the electric fields at the cell, the open time of the duty cycle of the electric field at the shutter grid is extended. After the background polarity has been switched to the opposite polarity, the open time is returned to its normal value.

5 Claims, 6 Drawing Sheets

METHOD AND AN APPARATUS FOR AN AIR SAMPLE ANALYSIS

FIELD OF THE INVENTION

The present invention relates to a system for an air sample analysis, and more particularly, to chemical agent monitors-detectors capable of monitoring and detecting chemicals of both polarities, and even more particularly, to improved chemical agent monitors-detectors, wherein the reset of the system to analysis of an air sample containing chemicals of opposite polarity does not upset the results of the analysis.

BACKGROUND OF THE INVENTION

Chemical agent monitors-detectors are known to be used for detection of chemical warfare agents for battlefield, for environmental clean-up, for treaty monitoring and verification missions, and for other purposes, where chemicals contained in the air are to be detected.

The chemical Agent Monitors ("CAMs") are employed by several armies as a reliable system for the above-described purposes.

The Improved Chemical Agent Monitor ("ICAM"), as best shown in FIG. 1, maintains the performance characteristics of the CAM but has an improved design which is even more reliable and maintainable.

A recently-developed Improved Chemical Agent Monitor-Detector ("ICAM-D") incorporates the ICAM to provide stand-alone detection capability using the proven, type-classified ICAM as the core of the detector. The ICAM becomes the sensor for the ICAM-D while the detector module provides command and control functions.

CAM, ICAM, ICAM-D and their modifications employ a dual polarity Ion Mobility Spectrometer ("IMS") as a sensor. In an IMS-based apparatus for an air sample analysis (CAM, ICAM, ICAM-D and the like) incoming gas from an inlet of the apparatus permeates a membrane and enters a drift tube. The drift tube houses a cell, which consists of an ionizing chamber (or reactor region), an electronic gate (or a shutter grid), and a drift region that terminates in an ion collector (or a charge collector).

Being introduced into the reactor region, the various molecules contained in the air sample are ionized by an ionizing source, and the ions of each polarity are separated by the electric field applied to the reactor region. It will be appreciated by those skilled in the art that certain electric fields are applied to all systems of the cell from a power source. An electric field applied to the shutter grid opens an entrance to the drift region only to ions of the polarity to be analyzed. Each species of the polarity being analyzed has a distinguishing ion mobility which determines a time of "flight" of the ions through the drift region to the charge collector. As each ion (or ion cluster) strikes the charge collector, it is represented as a peak in a collected current waveform. The collected charge produces a spectrum of the peaks in time. Each peak carries information regarding the identity and concentration of the chemical(s) being detected. Each peak is assessed by a microprocessor system programmed with a detection algorithm that recognizes the chemical and determines its concentration.

Despite the advantages of the CAM, ICAM, ICAM-D and their modifications developed recently, they all have a serious problem still unavoidable in dual polarity IMS-based detectors. This problem is associated with switching a polarity in the cell in order to analyze the chemicals of the opposite polarity. After the polarity in the system is switched, the previous ("old") background ions are replaced by the succeeding ("new") opposite polarity background ions. During the time that this replacement takes place, the "new" background ions lose their charge to the remaining background "old" background ions and are not available to contribute to the results of the analysis, thereby upsetting these results. Therefore, it would be highly desirable to overcome this disadvantage of the prior art, while enjoying high performance characteristics of the CAM, ICAM, ICAM-D and their modifications.

SUMMARY OF THE INVENTION

It is, therefore, an object of the present invention to provide a method for stabilizing equilibrium conditions associated with the switching of the polarity in the system for monitoring and detecting a chemical agent.

It is another object of the present invention to provide an improved apparatus for an air sample analysis, wherein the reset of the apparatus to the ions of different polarity does not upset the results of the analysis.

The present invention finds its particular utility in an apparatus for an air sample analysis, which comprises a cell including a reactor region, a drift region, a shutter grid separating the reactor region and the drift region, and a charge collector. The sample of air, containing molecules of different species, is introduced into the reactor region and the molecules are polarized, thereby producing ions of positive and negative polarities.

A potential gradient is applied across the cell, such that the ions of different polarities are separated, and the ions of the polarity to be analyzed move toward the drift region from the reactor region.

The type of the ions polarity to be analyzed (background polarity) is determined by the electric fields throughout the cell. By switching a polarity of the electric fields throughout the cell, applied to the reactor region, the shutter grid, the drift region and the charge collector, the ions of the opposite polarity can be measured, i.e. the background polarity is changed.

An electric field applied to the shutter grid either allows a pass to the drift region to ions of one of the positive and negative polarities or prevents these ions from entering the drift region. Controlling the electric field at the shutter grid, the ions of the background polarity are either encouraged to enter the drift region or are prevented from the same.

The ions of the background polarity to be measured arrive to the charge collector and produce a charge spectrum to be analyzed. The switching of the electric fields in the cell may influence a charge spectrum corresponding to the ions of the opposite one (a "new" one) of the said positive and negative polarities, thereby upsetting results of the sample analysis, since some ions of the "new" background polarity entering the drift region lose their charge to the remaining "old" background ions.

According to the teachings of the present invention, a method for stabilizing equilibrium conditions associated with the switching of the electric field in the cell, comprises the step of modulating a duty cycle of the electric field at the shutter grid. During the switching of the electric field at the shutter grid, the open time of the duty cycle is extended (the duty cycle including an open time and a closed time for ions of a certain polarity).

After the background polarity in the drift region has reached the opposite respective of said positive and negative polarities, the open time is returned to its normal value.

An apparatus for an air sample analysis, implementing the above-described method, includes a cell comprising a reactor region, a drift region, a shutter grid separating the reactor region and the drift region, a charge collector, and an improvement for stabilizing equilibrium conditions associated with the switching of the electric fields at the cell. The improvement comprises a means for modulating the duty cycle of the electric field at the shutter grid, thereby providing additional ions of said opposite one of said positive and negative polarities to enter the drift region and thereby more rapidly changing a background polarity in the drift region.

These and other objects of the present invention become apparent from a reading of the following specification taken in conjunction with the enclosed drawings.

DETAILED DESCRIPTION OF THE INVENTION

Figure 1:
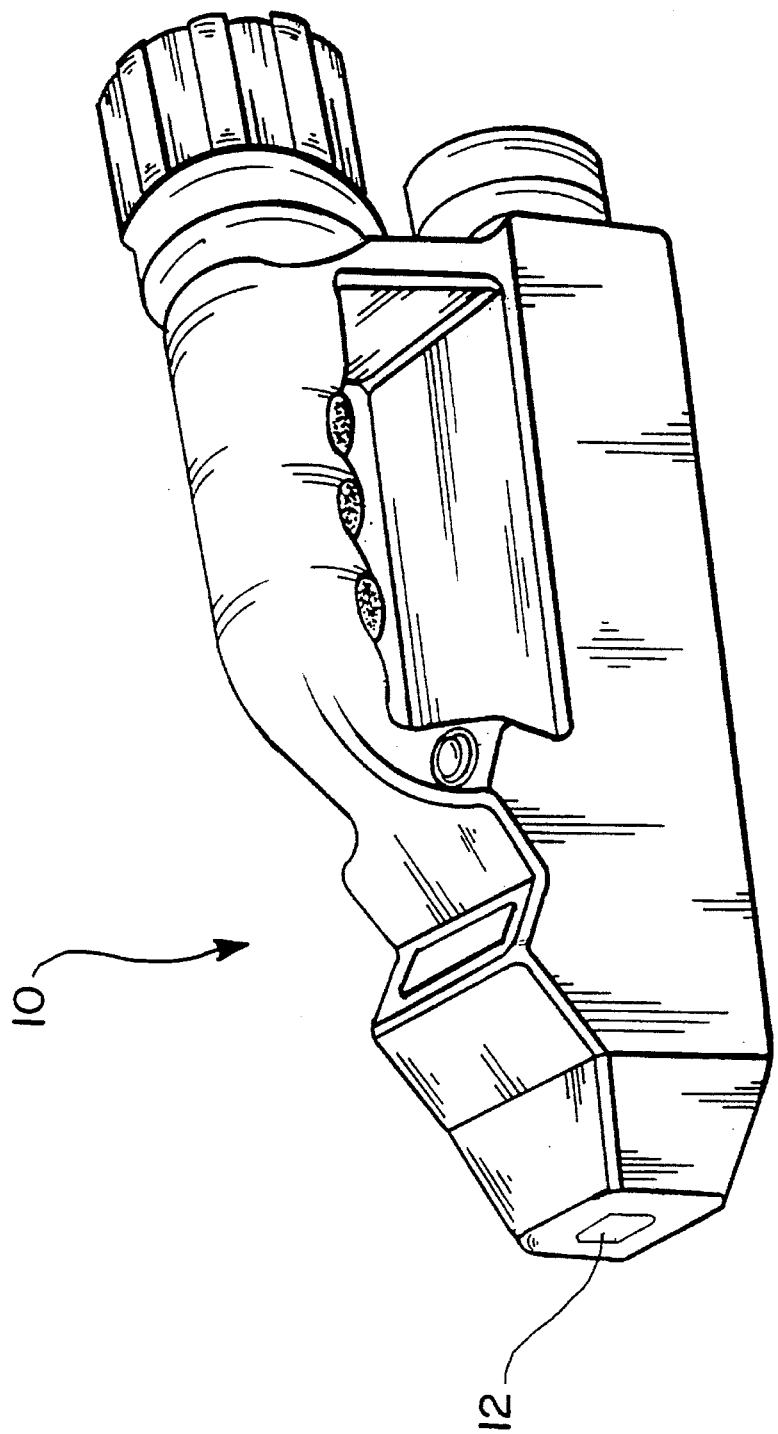
FIG. 1 is a perspective view of an apparatus for an air sample analysis (for instance, ICAM) of the prior art.
Figure 2:
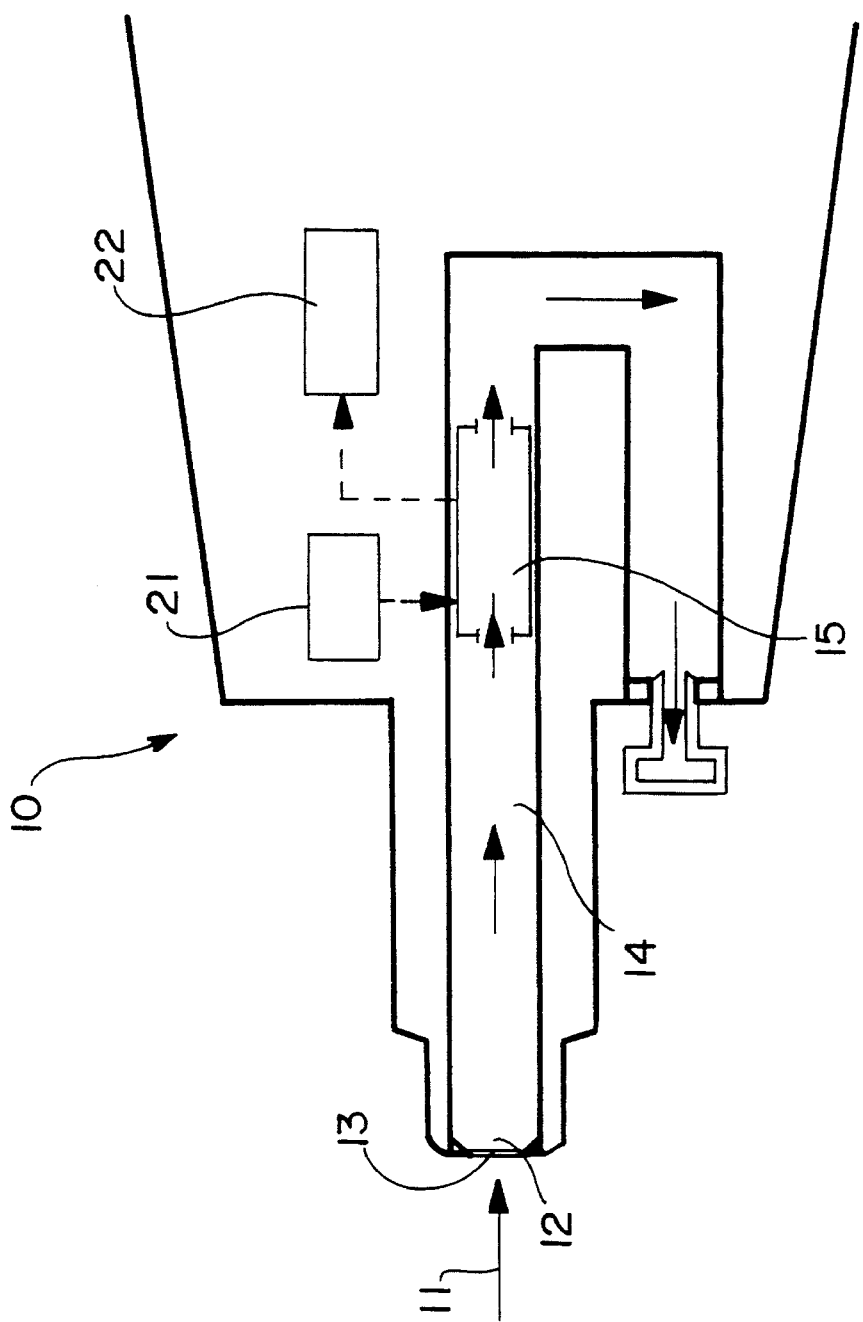
FIG. 2 shows somewhat schematically the operating principles of the apparatus of FIG. 1.
Figure 3:
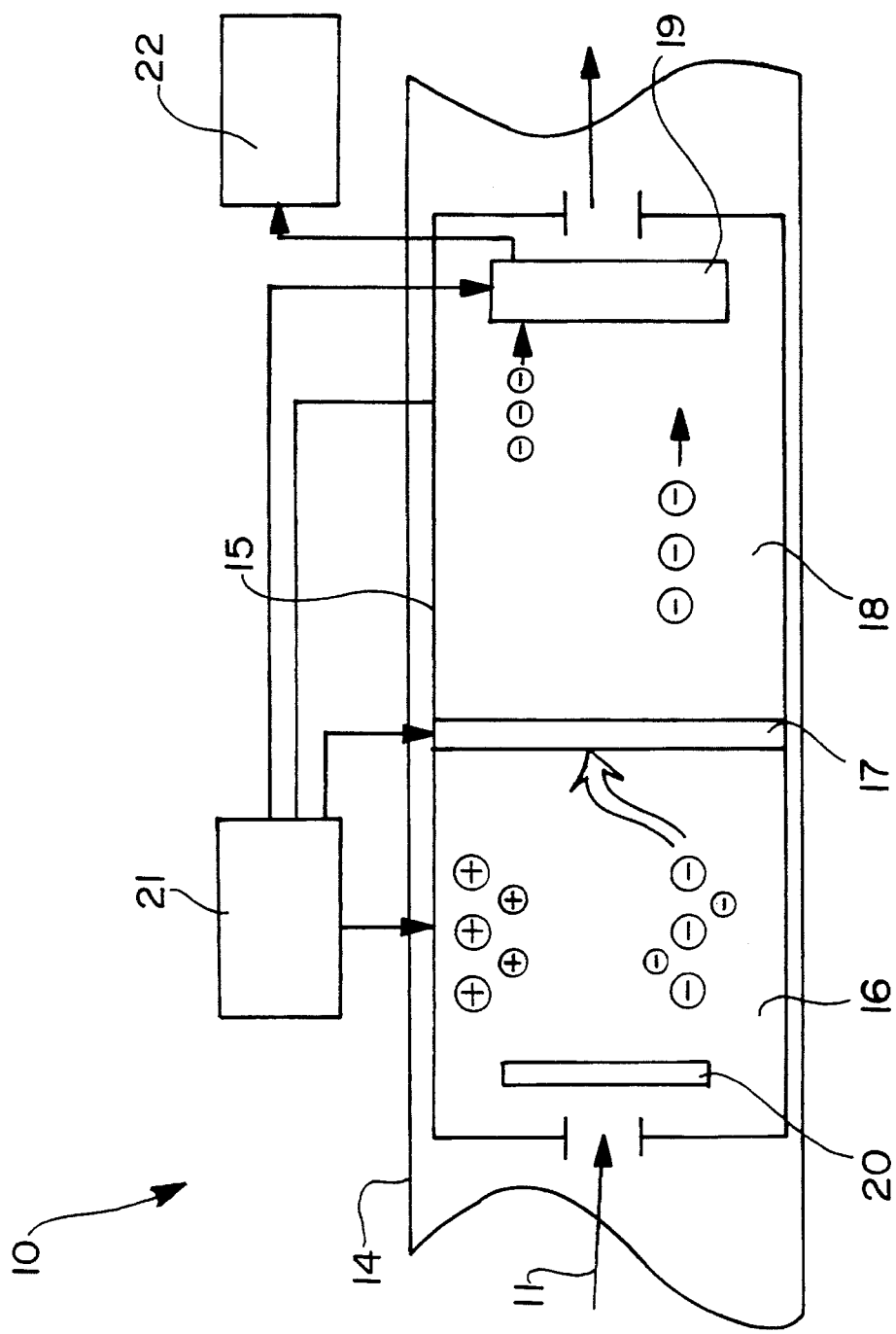
FIG. 3 shows the principles of Ion Mobility Spectrometry employed in the apparatus of FIG. 1.

As shown in FIGS. 1–3, in an IMS-based apparatus for an air sample analysis (CAM, ICAM, ICAM-D and the like) 10, incoming gas 11 from an inlet 12 of the apparatus 10 permeates a membrane 13 and enters a drift tube 14. The drift tube 14 houses a cell 15, which consists of an ionizing chamber (or reactor region) 16, an electronic gate (or a shutter grid) 17, and a drift region 18 that terminates in an ion collector (or a charge collector) 19.

Being introduced into the reactor region 16, the various molecules contained in the air sample 11 are ionized by an ionizing source 20, and the ions of each polarity are separated by the electric field applied to the reactor region 16. It will be appreciated by those skilled in the art that certain electric fields are applied to all systems of the cell 15 from a power source 21. An electric field applied to the shutter grid 17 opens an entrance to the drift region 18 only to ions of the polarity to be analyzed. Each species of the polarity being analyzed has a distinguishing ion mobility which determines a time of "flight" of the ions through the drift region 18 to the charge collector 19. As each ion (or ion cluster) strikes the charge collector 19, it is represented as a peak in a collected current waveform. The collected charge produces a spectrum of the peaks in time. Each peak carries information regarding the identity and concentration of the chemical(s) being detected. Each peak is assessed by a microprocessor system 22 programmed with a detection algorithm that recognizes the chemical and determines its concentration.

Figure 4:
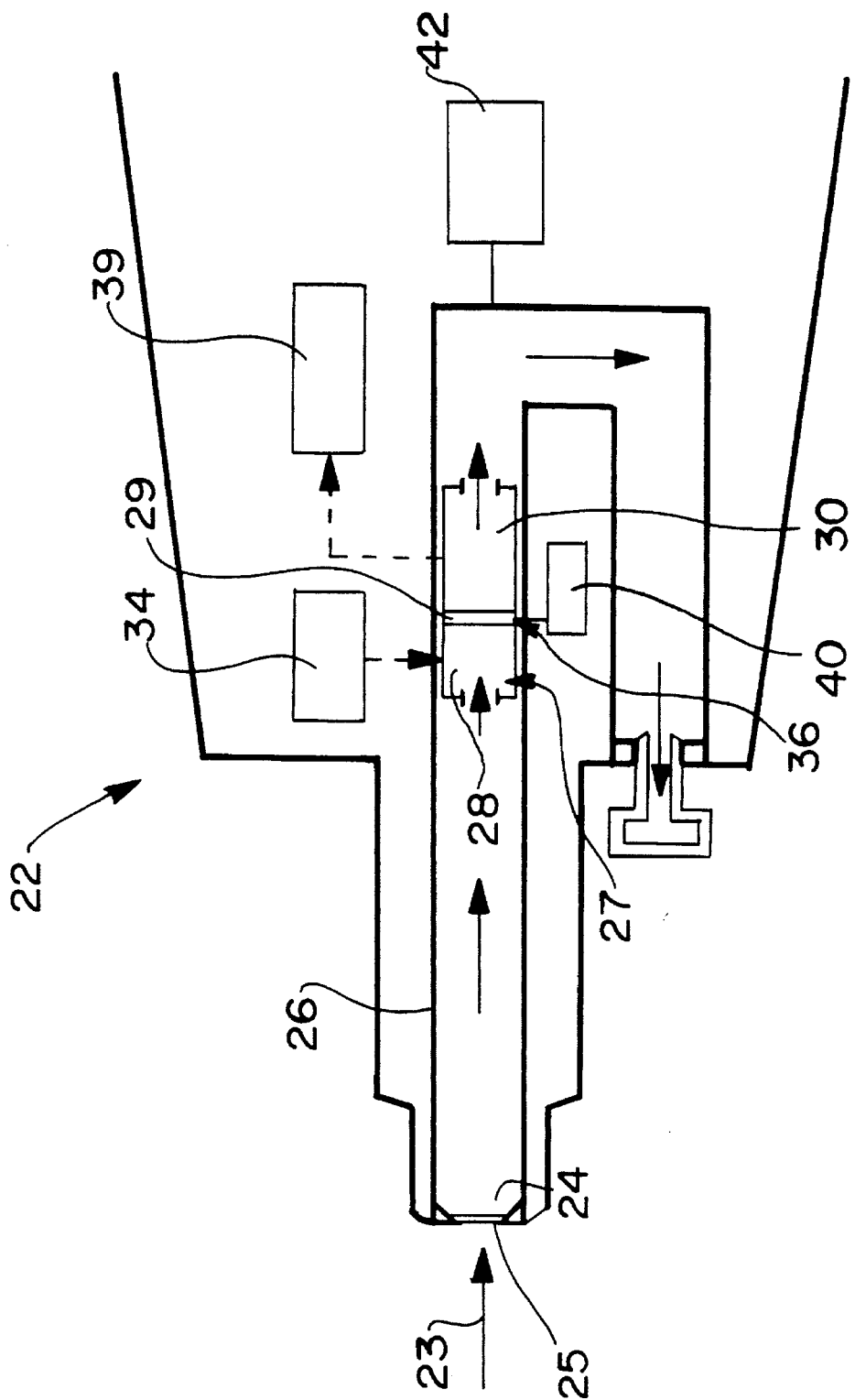
FIG. 4 shows schematically the operating principles of the apparatus of the present invention.
Figure 5:
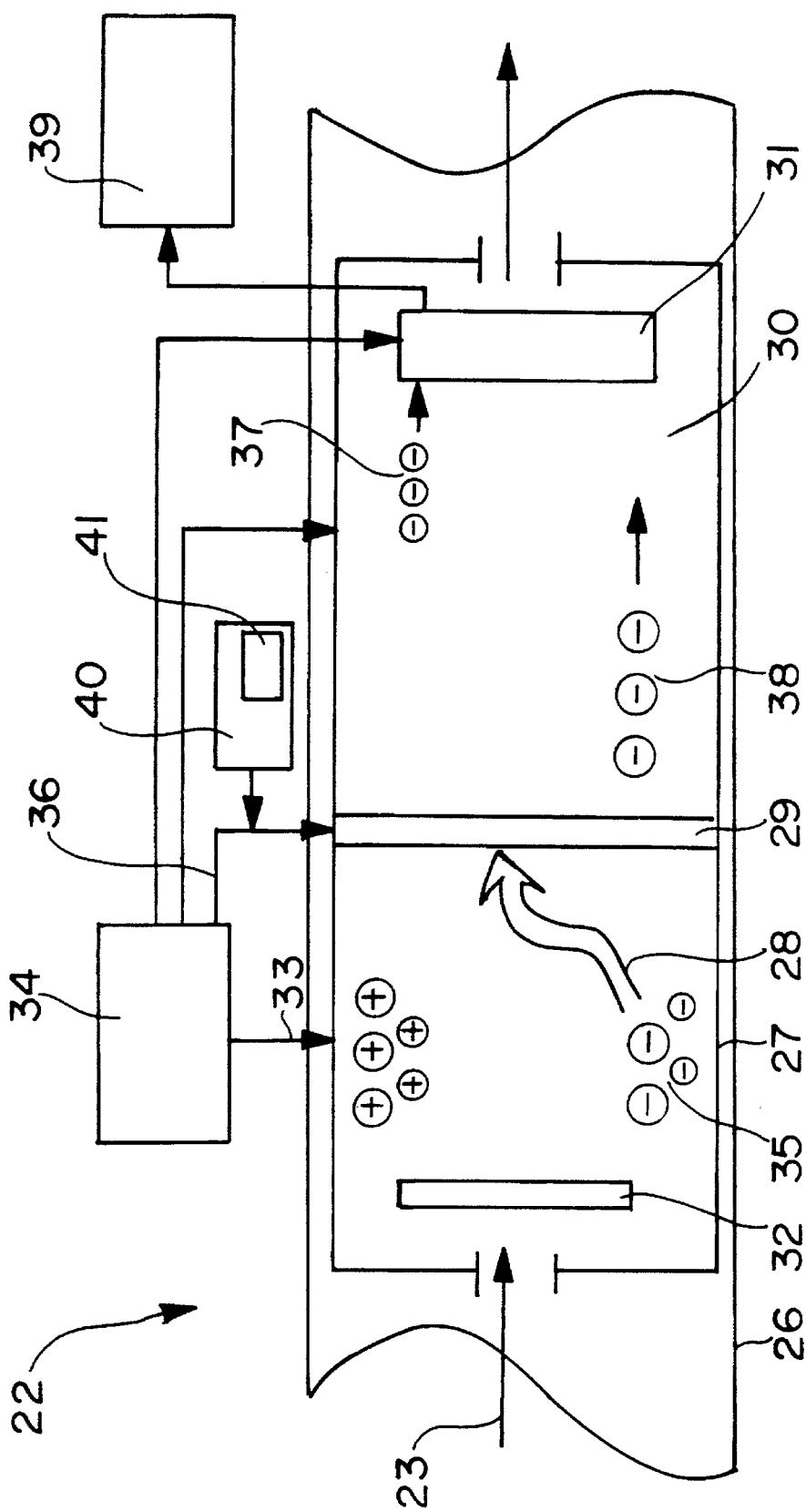
FIG. 5 shows schematically a cell (in enlarged scale) of the present invention.

With reference to FIGS. 4 and 5, the operating principle of an apparatus 22 for an air sample analysis (particularly, IMS-based systems) of chemicals is based on producing ions separating the ions, and counting the different types of the ions produced. In any IMS-based system, several key subsystems and components control the system performance. An incoming gas (or an air sample) 23 from an inlet 24 of the apparatus 22 permeates a membrane 25 and enters a drift tube 26. The drift tube 26 houses a cell 27, which consists of a reactor region 28, a shutter grid 29, and a drift region 30 that terminates in a charge collector 31.

The air sample 23 contains a relatively stable concentration of molecules of different species to be analyzed. Being introduced into the reactor region 29, the various molecules contained in the air sample 23, are ionized by an ionizing source 32, for instance, a radioactive foil plated with nickel $-63/10mC$ of Ni-63). The ions of each polarity are separated by the electric field 33 applied to the reactor region 28 from a power source 34. The ions 35 of the polarity to be analyzed move toward the drift region 30.

The drift region 30 is separated from the reactor region 28 by the shutter grid 29. The electric field 36 applied to the shutter grid 29 may either prevent the ions from entering the drift region 30, or the ions 35 to be analyzed are permitted to enter the drift region 30 by changing the field 36 of the shutter grid 29 for a short time interval, which is referred to as opening the shutter grid 29. Each species of the polarity being analyzed has a distinguishing ion mobility which determines a time of "flight" the ions through the drift region 20 to the charge collector 31. The ions of a lighter mass 37 accelerate more quickly and arrive to the charge collector 31 first, while ions with a greater mass 38 arrive to the charge collector 31 later in mass order. As each ion (or ion cluster) strikes the charge collector 31, it is represented as a peak in a collected current waveform. The collected charge produces a signature or spectrum of the peaks in time. Each peak is associated with a particular ion group. The relative position and magnitude of each peak carries information regarding the identity and concentration of the chemical(s) being detected. The peak time location with respect to the opening of the shutter grid 29 depends on the ions groups mobility. The area of each peak depends on the number of the ions in that group. The width of each peak depends on the arrival time variability within each ion group. The above spectrum features are also modified by all group's relative charge affinities and interactions between the different ion groups in the reactor region 28 and the drift region 30. As presented below, spectrum is also influenced by the detailed time history of the cell 27 voltages.

Each peak is assessed by a microprocessor system 39 programmed with a detection algorithm that recognizes peaks at specific locations. When a chemical is recognized, its presence and concentration is assessed against toxicity information stored in software memory, and the level is then indicated.

After a fixed number of air samples 23 are taken, a polarity change is made by switching all voltages supplied from the power source 34 to the cell 27. Switching the voltages permits the same physical cell 27 to analyze ions of the opposite polarity. The new voltage arrangement upsets the previous polarity equilibrium conditions. This upset produces a transient variation in the resulting signatures. The ion peaks immediately after switching are as low as 10% of the steady state (or of the equilibrium height). The first low amplitude pulses grow larger in successive signatures and eventually reach a stable equilibrium condition for the "new" polarity.

Figure 6A:
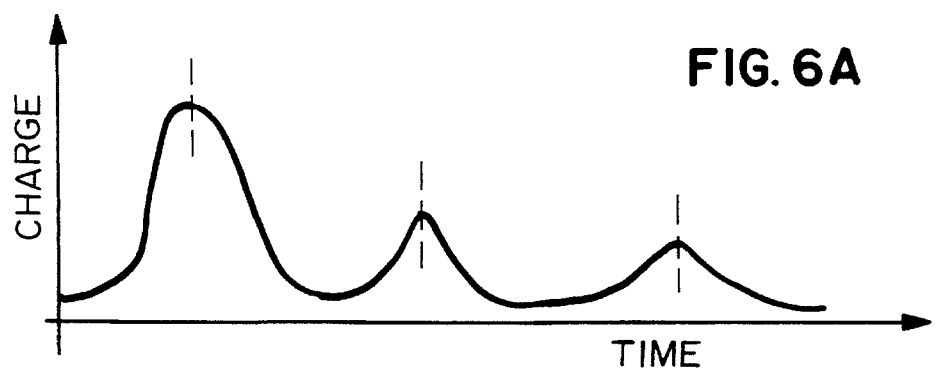
FIGS. 6A–6D are the graphical representations of the changes associated with the switching of voltages in the cell.
Figure 6B:
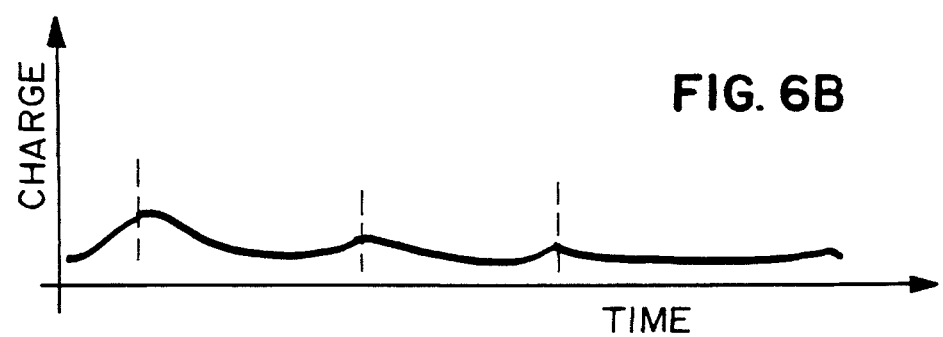
Figure 6C:
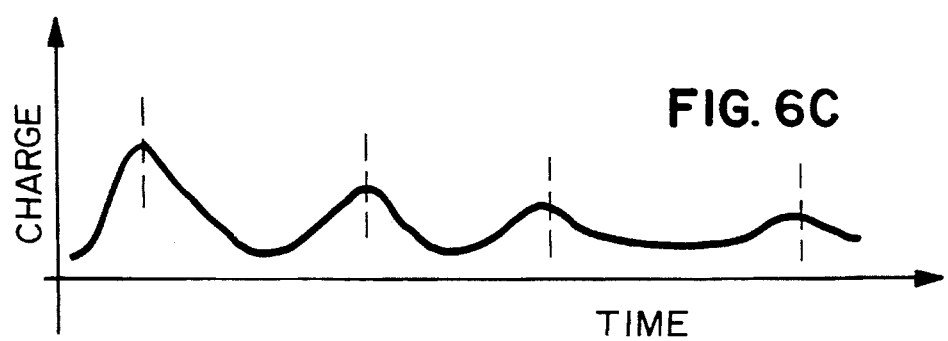
Figure 6D:
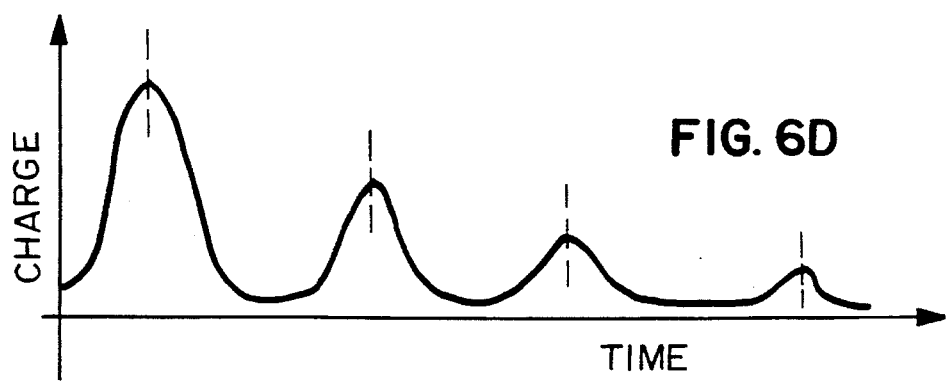

A graphical representation of the changes associated with the switching of voltages in the cell is best shown in FIGS. 6A–6D, representing selected signatures from a sequence of signatures produced by repeatedly opening the shutter grid 29. Particularly, FIG. 6A shows one of the positive and negative polarity ions final signature after conditions of that polarity have stabilized. FIG. 6B shows opposite one of the positive and negative polarity ions initial signature just after the voltage switching to the new polarity. FIG. 6C shows opposite one of the positive and negative polarity ions mid-way signature as new conditions have partially stabilized after voltage switching. FIG. 6D shows opposite one of the positive and negative polarity ions final signature as new conditions have stabilized.

It will be appreciated by those skilled in the art that the representations of FIGS. 6A–6D show different peak size, location and number which may occur with opposite polarity signatures. The representations show magnitude of the charge without considering sign. Ions of opposite charge would produce signatures of opposite polarity (not shown). The signatures after switching have the same general character as time progresses but they grow in size to the final stabilized value.

In addition to the ions producing signature peaks discussed above, there is a general background of ions in the drift tube 26. This background is not necessarily synchronized with the shutter grid 29 openings. The background ions produce a baseline current upon which the signature current peaks are superimposed. After the polarity is switched, the "old" polarity background ions are replaced by "new" polarity background ions.

During the time that this replacement takes place, some ions entering the drift region 30 lose charge to the remaining background ions of the opposite sign and are not available to contribute to the signature. As the background is converted to the new polarity, fewer charges are neutralized and the signature grows to its new equilibrium value.

In the IMS-based apparatus 22, the background ion change from "old" to "new" polarity, is speeded by modulating the duty cycle of the shutter grid 29. A control unit 40 is provided for modulating the electric field 36 applied to the shutter grid 29. The length of time required to change the background after polarity switching, depends on the density of new ions entering the drift region 30 as well as the elapsed time. During the background change, the shutter grid 29 is opened for a longer time than the normal signature sample interval. Additional ions introduced during the extended open time of the shutter grid 29, more rapidly change the drift region 30 to the new background ions. After the background has been changed to the new polarity, the open time of the shutter grid 29 is returned to the normal lower value, required for analysis. The signatures obtained at this point have stable amplitudes.

A software 41 of the control unit 40 controls the modified duty cycle of the shutter grid 29 and normally maintains fixed close and open time intervals during the switching mode. The control unit 40 (including the software 41) can be either an internal control unit (in this case a software used in the apparatus 10 of the prior art is to be changed), or to be an external control unit (the software of the prior art apparatus is not to be changed).

A synchronizing pulse synchronizes the control unit 40 timing with the internal operational timing of the apparatus 22. After a certain number of air samples (for instance, sixteen) are taken for a given polarity analyzes, the control unit 40 makes a polarity change request. As soon as the change request is activated, the control unit 40 sets the shutter grid 29 duty cycle to 50%, with the open time of the shutter grid equal to the time for sixteen samples. The 50% duty cycle provides extra open time of the shutter grid which speeds up the drift tube 26 background polarity change, thereby more rapidly producing equilibrium conditions.

A very dry vapor sample is required in the reactor region 28. A pneumatic system 42 is necessary to supply the dry air, transport the incoming molecules to the ionizing source 32, and remove the molecules from the cell 27 after discharge. The ICAM pneumatic system 42 consists of a pump and a sieve pack containing molecular sieve.

The pump contains two individual pumps pneumatically separated but mechanically connected and driven by a common motor. One of the pumps draws the sample in the inlet and the other pump supplies the internal airflow through the cell and sieve pack.

The sieve pack also provides vital functions in the detection system that far exceed its minor function of being a receptacle for the molecular sieve that keeps the cell dry and traps contaminants. In the ICAM, which uses a dopant chemistry to aid in interferant rejection and stabilize the cell reference, the sieve pack also contains the dopant permeation tube.

The pack contains a number of critical chambers that channel clean air to the cell and receive polluted air from the cell. It also serves as a mixing chamber for the dopant. The sieve pack also has a number of restrictors in various flow paths to control the relative pressure in the cell. Operating at a specific cell pressure is key to peak timing and algorithm recognition of the peaks.

The inlet 24 must gather the vapor to be analyzed and present the vapor to the membrane 25. The inlet 24 consists of a TEFLON® tube connected to the vacuum side of the pump. The tube outlet flares in a "wagon wheel" pattern to channel the vapor over the membrane 25. Vapors are then pulled through the pump and exhausted to the atmosphere. An inlet heater is used to ensure against agent hang-up on the TEFLON® surfaces.

The membrane 25 is an extremely important element in determining time of response and sensitivity. It must permit agent vapors to rapidly enter the cell while, at the same time, exclude as much moisture as possible.

The embodiment of the present invention (described herein) is intended for improvement of performance characteristics of the chemical agent monitor (CAM), Improved Chemical Agent Monitor (ICAM), Improved Chemical Agent Monitor-Detector (ICAM-D) and their modifications. However, the teachings of the present invention are equally applicable to any apparatus for an air sample analysis employing principles of dual polarity Ion Mobility Spectrometers (IMS).

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. In combination with an apparatus for an air sample analysis, wherein the apparatus includes a cell comprising a reactor region, a drift region, a shutter grid separating the reactor region and the drift region, and a charge collector, wherein the sample of air, containing molecules of different species, is introduced to the reactor region and the molecules are polarized, thereby producing ions of positive and negative polarities, the passive and negative polarities ions being separated, wherein electric fields applied to the cell determine a background polarity of ions to be analyzed, wherein an electric field applied to the shutter grid allows a pass to the drift region to ions of said background polarity, wherein, once the electric fields at the cell are switched, ions of opposite to said background polarity are to be analyzed, and the electric field at the shutter grid is switched to allow the ions of said opposite to said background polarity to enter the drift region, wherein the ions arrive at the charge collector and produce a charge spectrum to be analyzed, and wherein the switching of the electric fields at the cell may influence a charge spectrum corresponding to the ions of said opposite to said background polarity, thereby upsetting results of the sample analysis, a method for stabilizing equilibrium conditions associated with the switching of the electric fields at the cell, comprising the step of modulating a duty cycle of the electric field at the shutter grid, wherein the duty cycle includes an open time and a closed time for ions of a certain polarity, and wherein during the switching of the electric fields at the cell, the open time is extended.

2. The method of claim 1, wherein after the background polarity has been switched to said opposite to said background polarity, the open time is returned to its normal value.

3. In an apparatus for an air sample analysis, wherein the apparatus includes a cell comprising a reactor region, a drift region, a shutter grid separating the reactor region and the drift region, and a charge collector, wherein the sample of air containing molecules of different species is introduced to the reactor region and the molecules are polarized, thereby producing ions of positive and negative polarities to be separated, wherein electric fields applied to the cell determine a background polarity of ions to be analyzed, wherein an electric field applied to the shutter grid allows a pass to the drift region to the ions of said background polarity, wherein, once the electric fields at the cell are switched, ions of opposite to said background polarity are to be analyzed, and the electric field at the shutter grid is switched to allow the ions of said opposite to said background polarity to enter the drift region, thereby switching the background polarity to an opposite background polarity in the drift region, wherein the ions arrive to the charge collector and produce a charge spectrum to be analyzed, and wherein the switching of the electric fields at the cell may influence a charge spectrum corresponding to the ions of said opposite to said background polarity thereby upsetting results of the sample analysis, an improvement for stabilizing equilibrium conditions associated with the switching of the electric fields at the cell, comprising means for modulating a duty cycle of the electric field at the shutter grid, the duty cycle including an open time and a closed time for ions of a certain polarity, and wherein during the switching of the electric fields at the cell, the open time is extended, thereby providing additional ions of said opposite to said background polarity to enter the drift region and thereby more rapidly changing a background polarity in the drift region to the opposite to said background polarity.

4. The improvement of claim 3, wherein after the background polarity has been switched to said opposite to said background polarity, the open time is returned to its normal value.

5. In an ion mobility spectrometer for analysis of ions of background and opposite polarities, wherein electric fields at a cell determining the background polarity of ions to be analyzed are switched to determine the opposite polarity of ions to be analyzed, wherein an electric field applied to a shutter grid has a duty cycle and is switched to allow a pass to the ions of the opposite polarity, thereby defining an open time of said duty cycle for the ions of the opposite polarity, the improvement comprising first means operative during switching of the electric fields at the cell for extending the open time of the duty cycle of the electric field at the shutter grid during switching the ions to the opposite polarity, and second means operative upon switching the ions to the opposite polarity at the cell for returning the open time of the duty cycle of the electric field at the shutter grid to its normal value.

* * * * *